United States Patent
Jaynes

(10) Patent No.: US 7,803,755 B2
(45) Date of Patent: Sep. 28, 2010

(54) MOLECULES FOR THE TREATMENT AND PREVENTION OF FUNGAL DISEASES

(76) Inventor: Jesse Jaynes, 1583 Overhill Ct., Auburn, AL (US) 36830

(*) Notice: Subject to any disclaimer, the term of this patent is extended or adjusted under 35 U.S.C. 154(b) by 678 days.

(21) Appl. No.: 11/643,402

(22) Filed: Dec. 21, 2006

(65) Prior Publication Data

US 2008/0153748 A1    Jun. 26, 2008

(51) Int. Cl.
A61K 38/00 (2006.01)
A61K 38/16 (2006.01)
A61K 38/10 (2006.01)

(52) U.S. Cl. .............................. 514/2; 514/12; 514/13; 514/14

(58) Field of Classification Search ..................... None
See application file for complete search history.

(56) References Cited

U.S. PATENT DOCUMENTS 5,561,107 A * 10/1996 Jaynes et al. ................... 514/12
6,514,692 B2    2/2003 Jaynes
7,288,622 B1 * 10/2007 Jaynes et al. ................ 530/300

FOREIGN PATENT DOCUMENTS

WO    WO 95/28832    * 11/1995

OTHER PUBLICATIONS

Ma et al. ("Inhibitory Activity of Synthetic Peptide Antibiotics on Feline Immunodeficiency Virus Infectivity In Vitro," J. Virology, 2002, 76, 9952-9961).*

Oard et al. ("Characterization of antimicrobial peptides against a US strain of the rice pathogen Rhizoctonia solani," J. Applied Microbiology, 2004, 97, 169-180).*
Jacobi et al. ("In vitro toxicity of natural and designed peptides to tree pathogens and pollen," Canadian Journal of Botany, 2000, 78, 455-461).*
De Lucca et al. ("Fungicidal properties, sterol binding, and proteolytic resistance of the synthetic peptide D4E1," Canadian J. Microbiology, 1998, 44, 514-520).*
Ballweber et al. ("In Vitro Microbicidal Activities of Cecropin Peptides D2A21 and D4E1 and Gel Formulations Containing 0.1 to 2% D2A21 against Chlamydia trachomatis," Antimicrobial Agents and Chemotherapy, 2002, 46, p. 34-41).*
Rioux et al. ("Structural changes of spores of tree fungal pathogens after treatment with the designed antimicrobial peptide D2A21," Canadian Journal of Botany, 2000, 78, 462-471).*
CAS 2004:639493.*
Cary J.W et al. 2000. Transgenic expression of a gene encoding . . . Plant Science 154: 171-181.
Robertson C. N . et al. 1998. Peptidyl membrane-interactive molecules . . . World J. Urol. 16: 405-409.
Badkar. A.T. et. al. 2000. In vitro release testing of a peptide gel. Pharmaceutical Technolgoy. Abstract.
Schwab. U. et al. 1999. In vitro Activities of Designed antimicrobials..Antimicrobial Agents and Chmotherapy 43 (6): 1435-1440.

* cited by examiner

*Primary Examiner*—Christina Bradley
(74) *Attorney, Agent, or Firm*—Dodds and Associates; John Dodds; L. Susanne Somersalo

(57) ABSTRACT

This disclosure provides a method and a product to treat fungal nail infections and Athlete's foot in a fast and non expensive way. The product contains one or more lytic peptides in water solution.

9 Claims, No Drawings

MOLECULES FOR THE TREATMENT AND PREVENTION OF FUNGAL DISEASES

SEQUENCE DATA

This application contains sequence data provided on a computer readable diskette and as a paper version. The paper version of the sequence data is identical to the date provided on the diskette.

BACKGROUND OF THE INVENTION

1. Field of Invention

The present invention relates to the field of curing and treating fungal diseases. More specifically the invention relates to peptide compounds efficiently preventing and treating nail fungus and Athlete's foot.

2. Background

The bases for nail fungus and Athlete's foot are fungal diseases known as onychomycosis and *tinea pedis* (also, *tinea cruris* (Jock Itch); and, *tinea corporis* (Body Ringworm) would be treatable). Onychomycosis is the number one diagnosed and treated disease by podiatrists today. It is present in 2 to as high as 5 percent of the population with the most common source of contamination coming from the patients own skin. It has been reported that as much as 70 percent of the population has fungus recovered from the feet. Fifteen to 20 percent of people between the ages of 40 and 60 have onychomycosis, 32 percent of 60- to 70-year-olds have nail fungus and approximately 50 percent of those over 70 are afflicted. Conservatively, it is estimated as many as 17 million people in the U.S. and 300 million worldwide suffer from nail fungus, and 51 million people in the U.S. and 900 million worldwide suffer from Athlete's foot. Combined those adds up to 68 million who suffer from these two diseases within the U.S. and 1.2 billion worldwide.

Many people don't realize they have a fungal nail problem. Moreover, many do not seek treatment. Still, fungal toenail infections are a common foot health problem. Such infections can persist for years without ever causing pain. The disease, characterized by a change in a toenail's color, is often considered nothing more than a mere blemish, but it can present serious problems if left untreated.

Onychomycosis fungal nail infections are created underneath the surface of the nail, which can also penetrate the nail. In addition to causing difficulty and pain when walking or running, fungal nail infections are often accompanied by a secondary bacteria land/or yeast infection in or about the nail plate.

A group of fungi called dermophytes easily attack the nail, thriving off keratin, the nail's protein substance. When the tiny organisms take hold, the nail may become thicker, yellowish-brown or darker in color, and foul smelling. Debris may collect beneath the nail plate, white marks frequently appear on the nail plate, and the infection is capable of spreading to other toenails, the skin, or even the fingernails.

Nail bed injury may make the nail more susceptible to all types of infection, including fungal infection. Those who suffer chronic diseases, such as diabetes, circulatory problems, or immune-deficiency conditions, are especially prone to fungal nails. Other contributory factors may be a history of Athlete's foot and excessive perspiration. The problem is particularly acute among older adults.

There are five basic ways to treat this problem. You can treat it with debridement (removal of the devitalized or contaminated tissue); superficial surgical nail avulsion; topical medications; oral medications; or, a combination of oral and topical medications. Depending on the type of infection persons have, over-the-counter liquid antifungal agents, while sometimes effective, may not prevent a fungal infection from recurring. A topical or oral medication may need to be prescribed, and the diseased nail matter and debris removed by a process called debridement. In some cases, surgical treatment is prescribed, during which the infected nail is removed. Permanent removal of a chronically painful nail, which has not responded to any other treatment, permits the fungal infection to be cured, and prevents the return of a deformed nail, naturally, this is viewed as a last resort.

Athlete's foot (*tinea pedis*) is a skin disease caused by a fungus, usually occurring between the toes. The fungus usually attacks the feet because shoes create a warm, dark, and humid environment that encourages fungal growth. The warmth and dampness of areas around swimming pools, showers, and locker rooms, are also breeding grounds for fungi. Not all fungus conditions lead to Athlete's foot, however. Other conditions, such as malfunctions of the sweat mechanism, reaction to dyes or adhesives in shoes, eczema, and psoriasis, also may mimic Athlete's foot.

Symptoms of athlete's feet include drying skin, itching, scaling, inflammation, and blisters. Athlete's foot may spread to the soles of the feet and to the toenails, and can spread to other parts of the body, including the groin and underarms. While fungicidal and fungistatic chemicals are usually used to treat Athlete's foot problems, they often fail to contact the fungi in the horny layers of the skin. Instead, podiatrists may prescribe topical or oral antifungal drugs.

Currently the products available for treating and preventing nail fungus and athlete's foot include products under market names LAMISIL, PENLAC, NAFTIN and SPECTAZOLE.

LAMISIL is an oral terbinafine product in tablet form being used to cure nail fungus. It requires pulse-dosing terbinafine (250 mg/d) for at least seven days every three months. Some applications have run as long as every four months, often with adverse drug effects (liver damage), and at high cost for patients and medical insurance providers.

PENLAC utilizes Ciclopirox as its principal ingredient. It is applied topically with a small brush and is promoted as being effective against mild to moderate nail infections. It takes up to one year for healthy treated toe nails to grow in, and about half that time for fingernails. Ciclopirox nail lacquer 8% is the only currently approved topical nail treatment effective in treating onychomycosis. Ciclopirox lacquer is approved for mild to moderate onychomycosis of the finger or toenails. It is a hydroxypridone with a unique mechanism of action. It works by chelating the polyvalent cations ($Fe^{+3}$ or $Al^{+3}$), resulting in the inhibition of metal dependent enzymes that degrade the toxic peroxides within the fungal cell. The package insert suggests applying the drug once a day for 48 weeks to the infected nails or until a clinical cure has been achieved. The manufacturer also suggests monthly debridements of the nail done by healthcare professional and weekly debridements by the patient to remove excessive fungal material. The drug has antibacterial and anti-inflammatory activity as well as a wide spectrum of activity against fungus. The drug has been used as a conservative first-line drug or for patients who have physical or psychological concerns with oral medications. Although mycological cure rates have been good (47 to 86 percent), the clinical cure rates are approximately one-half to one-quarter that of the oral medications.

Even with the lower cure rates, 90 percent of patients rate their onychomycosis as "improved" after using ciclopirox lacquer. Ciclopirox has the best safety profile of all current FDA approved drugs for onychomycosis.

NAFTIN is a naftifine hydrochloride (1%) based antifungal product that is marketed in both a gel and cream form. It is has a rather high ethyl alcohol content of 52% by weight. It may pose irritation to the skin and nausea and vomiting if ingested. Naftifine hydrochloride is a synthetic allylamine derivative that has been shown to exhibit fungicidal activity in vitro against a wide spectrum of organisms, including *Trichophyton rubrum, Trichophyton mentagrophytes, Trichophyton tonsurans, Epidermophyton floccosum, Microsporum canis, Microsporum audouini*, and *Microsporum gypseum*, and fungistatic activity against *Candida* species, including *Candida albicans*.

SPECTAZOLE is largely used for dermatological purposes against such fungus as *Tinea pedis* (Athlete's Foot); *Tinea cruris* (Jock Itch); and, *Tinea corporis* (Body Ringworm).

Accordingly, there is a clear need for a topical treatment that would be effective on variety of microbes causing nail disorders, itching and inflammation. The currently available topical treatments have only a limited efficacy on a limited number of microbes and additionally the treatment times are long and therefore the treatment is also expensive. The present disclosure therefore aims to solve the problems currently encountered with the products available.

Accordingly, an object of the present disclosure is to provide a composition to effectively and fast attack a number of microbes causing nail disorders and Athlete's foot.

Another object of the present disclosure is to provide a number of peptide molecules that are effective in treating and preventing fungal nail infections and athlete's foot.

An even further object of the present disclosure is to provide a treatment that is effective against Onychomycosis.

A yet another object of the present disclosure is to provide a treatment that is effective against microbes such as *Trichophyton rubrum, Trichophyton mentagrophytes, Trichophyton tonsurans, Epidermophyton floccosum, Microsporum canis, Microsporum audouini, Microsporum gypseum*, and *Candida* species, including *Candida albicans*.

Another object of the present disclosure is to provide an effective treatment for fungal nail infections and athlete's foot that is more affordable than the existing treatments.

DETAILED DESCRIPTION OF THE INVENTION

Over the last 20 years, a great deal of information has been published describing naturally occurring peptides that possess antibiotic activity (113-17). Hundreds of these so-called lytic peptides have been characterized, with numerous variations added to the structural repertoire by design (18-22). These molecules are small basic proteins that appear to be major components of the antimicrobial defense systems of a number of animals including insects, amphibians, and mammals (23-25). They have also been found in numerous plant species and have even been found in some types of bacteria (26-28). They exist in a range of sizes and virtually all have the potential to form amphipathic alpha-helices or partial beta-pleated sheets that are locked in this conformation by formation of specific disulfide linkages, all types interacting with most cells at their membrane surfaces.

By inspection of the physical properties of those naturally occurring peptides containing no more than two cysteine residues, we suggest that they can be catalogued into one of three distinct alpha-helical classes (unpublished data). More than 90% of these types of natural peptides conveniently fall within this classification system consisting of different arrangements of highly cationic amphipathic and hydrophobic regions (29-40). Representative examples of natural peptides in this organizational system are melittin—class 1 (amphipathic region is C-terminal and the N-terminal region comprises a hydrophobic tail), cecropins—class 2 (hydrophobic tail at the C-terminus while the N-terminal region is amphipathic, mirror image of class 1), and magainins—class 3 (more or less amphipathic the full length of the molecule). Defensins and similar peptides (containing more than two cysteine residue) exist as beta-sheet peptides and do not fall into these kinds of class distinction.

These physical characteristics have guided our efforts in peptide design for the last 15 years. We have generated a great deal of data from extensive in vitro and in vivo experiments during this time and have come to appreciate the range and complexity of the cellular interactions of these molecules (33-38). Perhaps, in some respects, the so-called "lytic" activity of these peptides is the least important of their capabilities (unpublished results).

We have designed more than 30,000 separate synthetic peptides and tested more than 300 of these designs in order to help determine the structural features relevant to the control and treatment of diseases in plants, animals, and humans. The more important physical criteria of the peptides are: 1) degree of amphipathy, 2) length of amphipathy, 3) heterogeneity of amphipathic section, 4) placement of amphipathic section (N or C terminal), 5) positive charge density (less or more), 6) hydrophobicity of amphipathic section, 7) presence of hydrophobic tail, 8) length of hydrophobic tail, 9) hydrophobicity of tail, 10) placement of hydrophobic tail (N or C terminal, 11) absence or presence (and position of) of positive charged center, 12) absence or presence (and position of) of flanking sequence, 13) predominating secondary structure, 14) termini modification (N-acetylation, C-amidation), 15) surface area of hydrophilic and hydrophobic faces and 16) steric or volume considerations.

Antimicrobial Peptides as Topical Microbicides

Antimicrobial peptides are small effector molecules with broad distribution at tissue sites initially exposed to microbial invasion [1,2]. These peptides are produced by several cell types including phagocytes and epithelial cells, including those within the vaginal and endocervical mucosa [1,2]. Epithelial expression may be both constitutive and inducible [3] with efficacy against bacteria, fingi, protozoa, tumor cells, and enveloped viruses (including HIV) [4,5]. Consistent features of microbial peptides are their small size (12-100 amino acids in length), amphipathic secondary structure associated with an alpha helix or beta pleated sheet, and polycationic charge. The mechanism of action of antimicrobial peptides is not fully understood however direct antiviral effects occur at concentrations well below that necessary to cause any observable cellular effect (unpublished data). Peptide-lipid interactions lead to membrane permeabilization [6] and there is data to support that this occurs by an electrostatic charge-based mode of action rather than pore formation [7,8].

Synthetic analogues to natural microbicidal peptides such as defensins and magainins have been designed based on modulating sequence, secondary structure and other properties of naturally occurring alpha helical and beta pleated sheet peptides. These synthetically derived antimicrobials have been shown to have potent antiviral effects in vitro against FIV and HIV (detailed in preliminary data), herpes simplex virus (HSV) [9], *Chlamydia trachomatis* [10] and *Neisseria gonorrhea* (unpublished data). In addition, vaginal application of synthetic antimicrobial peptides prevents infection by *Trichomonas vaginalis* [11]. However, synthetic antimicrobial peptides proposed for use against vaginal lentivirus transmission have also been shown to spare *Lactobacilli* species thus demonstrating selective antimicrobial activity [12].

The treatment according to this invention is called FUNGALL. FUNGALL is very effective against fungal nail infections (onychomycosis) and athlete's foot (*tinea pedis*). The active ingredient of the product according to this invention is a synthetically designed peptide molecule of the class known as "lytic peptides" or Antimicrobial peptides". According to a preferred embodiment the peptide is selected from the sequences listed in Table 1. The peptides according to the sequences in Table 1 have been designed for optimal antifungal activity. However, other natural or synthetic peptides with similar structure can also be used.

The use of FUNGALL provides almost immediate relief to patients suffering from fungal nail infections or athlete's foot as compared to currently commonly used products involving cream or pill therapies. The product is applied topically by the podiatrist. Application of the product only requires two or three treatments within a single week to effectuate a cure and complete destruction of the fungus—both as it relates to its use against nail fungus or Athlete's foot. In the case of Athlete's foot the product provides almost immediate relief from the itching caused by the pathogen.

No known side-effects have been noted or demonstrated as a result of its use topically. In addition to its ability to kill the fungus, the product also is likely to simultaneously contribute two additional benefits: 1) Protection for the treated area against attack by other opportunistic pathogens; and 2) Accelerated healing of the area that may have been damaged by the pathogen.

Unlike all the other products currently being marketed for use against fungal nail infections and Athlete's foot, the product according to this disclosure can bring almost immediate relief (requiring only two or three applications within a week, and healthy nail recovery within less than a month) with no adverse side-effects, and at a much lower cost. In addition, the product of this disclosure will save the patient considerable time and prolonged discomfort. The product according to this disclosure also demonstrates a strong antibacterial and anti-inflammatory activity, and is very likely to prove very effective on a rather broad range of other pathogenic microorganisms.

TABLE 1

Amino acid sequences of the lytic peptides efficient to treat fungal nail infections and Athlete's foot.

| SEQ ID NO | Amino acid sequence |
|---|---|
| 1 | AFKKAFKKAKKAFKKAFKAFAFA |
| 2 | FAKRFVKKFRRFIKKFLRFAFVF |
| 3 | FAKKFAKKFKKFAKKFAKFAFAF |
| 4 | FKLRAKIKVRLRAKIKL |
| 5 | FKLRAKIKVRLRAKIKLGPGRFKLRAKIKVRLRAKIKL |
| 6 | FRVKARIRLKVKARIRL |
| 7 | FRVKARIRLKVKARIRLGPGRFRVKARIRLKVKARIRL |
| 8 | RGDGGGGFRVKARIRLKVKARIRL |
| 9 | FRVKARIRLKVKARIRLKRKR |
| 10 | RGDFRVKARIRLKVKARIRL |
| 11 | AVKRVGRRLKKLARKIARLGVAKLAGLF |
| 12 | MCKLRFRGPGRIKVRLC |
| 13 | KKFAKKFKKFAKKFAKFAKKFAFAF |
| 14 | KKFAKKFKKFAKKFAKFAFAF |
| 15 | FAFAFKKAFKAFKKAFKKFKKAFKK |
| 16 | FAFAFKAFKKAFKKFKKAFKK |
| 17 | FAFAFKAFKKAFKKFKKAFKKAF |
| 18 | AFAFAKFAKKFAKKAKKFAKKFA |
| 19 | FVFAFRLFKKIFRRFKKVFRKAF |
| 20 | FAFAFKAFKKAFKKFKKAFKKAFGPGRFAKKFAKKFKKFAKKFAKFAFAF |
| 21 | AFAFKKAFKAFKKAFKKFKKAFKKGPGRKKFAKKFKKFAKKFAKFAKKFAFAF |
| 22 | FAFAFKAFKKAFKKFKKAFKKGPGRKKFAKKFKKFAKKFAKFAFAF |
| 23 | AFAFAKFAKKFAKKAKKFAKKFAGPGRAFKKAFKKAKKAFKKAFKAFAFA |

TABLE 1-continued

Amino acid sequences of the lytic peptides efficient to
treat fungal nail infections and Athlete's foot.

| SEQ ID NO | Amino acid sequence |
|---|---|
| 24 | FVFAFRLFKKIFRRFKKVFRKAFGPGRFAKRFVKKFRRFIKKFLRFAFVF |
| 25 | FAKKFAKKFKKFAKKFAKFAFAFGPGRFAFAFAFKAFKKAFKKFKKAFKKAF |
| 26 | FRVKARIRLKVKARIRLGPGRFRVKARIRLKVKARIRL |
| 27 | FRVKARIRLKVKARIRLGPGRFAKRFVKKFRRFIKKFLRFAFVF |
| 28 | NCGPCKGGGGKKFAKKFKKFAKKFAKFAKKFAFAF |
| 29 | KKFAKKFKKFAKKFAKFAKKFAFAFGGGGNCGPCK |
| 30 | AFAFKKAFKAFKKAFKKFKKAFKKGPGRKKFAKKFKKFAKKFAKFAKKFAFAFC |
| 31 | WFKKAFKKAKKAFKKAFKAFAFA |
| 32 | FLFAFRIFKRVFKKFRKLFKRAF |
| 33 | MGCKLRFRGPGRIKVRLC |
| 34 | MGFKLRAKIKVRLRAKIKL |
| 35 | MGFRVKARIRLKVKARIRL |
| 36 | MGFKLRAKIKVRLRAKIKLGPGRMGFKLRAKIKVRLRAKIKL |
| 37 | MGFRVKARIRLKVKARIRLGPGRMGFRVKARIRLKVKARIRL |
| 38 | CVOLFPVOLFPC |
| 39 | CVKLFPVKLFPC |
| 40 | COLFPFFDEYVC |
| 41 | CKLFPFFDEYVC |
| 42 | CKLRFRGPGRIKVRLC |
| 43 | CKLRFRIKVRLC |
| 44 | CPGFAKKFAKKFKKFAKKFAKFAFAF |

EXAMPLE I

Treatment of Infected Nail

In the case of infected nails, the nail is preferably roughed with an emery board or nail file to help facilitate the absorption of the product. Using the eye dropper, enough products sufficient only to cover the infected area is used. The procedure is repeated by the podiatrist at least three times within a single week. The infected nail itself may take a couple of weeks to completely rejuvenate to normal healthiness that can be determined by examination by the podiatrist.

EXAMPLE II

Treatment of Athlete's Foot

The peptide is diluted with distilled water so that the end concentration of the peptide is between 1 and 100 μM and preferably approximately 75. A few drops of the peptide solution is placed on the infected area and slightly beyond with a wet cotton ball and allowed to air dry.

The patient will realize almost immediate relief from the normal itching sensation that normal accompanies athlete's feet. Two or three treatments within a period of one week result in the destruction of the fungus altogether, and healthy skin growth is evident within a day or two following the final application of the product.

EXAMPLE III

Preparation of the Product for Use

According to a preferred embodiment the product of this invention is provided in a small brown bottle whose lid is a screw-topped eye-dropper, which is used to actually apply the product. According to this embodiment the bottle contains a preparation of one or more lytic peptides selected from table 1. The product is to be held or stored under normal refrigeration (40 degree F.) until ready for use. It also is not to be subjected to prolonged daylight. When ready for use, the eye-dropper lid is removed and distilled or bottled water is added to the specific level indicated on the bottle, so as to provide preferred concentration of about 75 μM of the peptide. Tap water should never to be used due to the normal impurities found in it. Once the distilled or bottled water has been added to the product, it should again be stored under normal refrigeration, and used within about a ten (10) day period.

EXAMPLE IV

Treatment of Onychomycosis

About 200 patients diagnosed with onychomycosis used the composition according to this disclosure under instructions of a certified podiatrist. Approximately 80% of the patients were found to have significant improvement in the appearance of the nail. Some patients reported that the nails did not heart as much after the treatment. Some patients have experienced a complete cure and others are in process of treatment. Generally the nail looks lighter than and not as thick as before treatment. The treatment was more effective on nails where the infection is in its beginning. On nails where the fungus is completely involved the treatment is not quite as effective, however even when applied on such nails the nail becomes softer and more easily to debride.

While the invention has been particularly shown and described with the reference to the preferred embodiment thereof, it will be understood by those skilled in the art that various changes in form and details may be made without departing from the spirit and scope of the invention.

LITERATURE CITED

1. Quayle A J, Porter E M, Nussbaum A A, et al. Gene expression, immunolocalization, and secretion of human defensin-5 in human female reproductive tract. Am J Pathol 1998, 152:1247-1258.
2. Valore E V, Park C H, Quayle A J, Wiles K R, McCray P B, Jr., Ganz T. Human beta-defensin-1: an antimicrobial peptide of urogenital tissues. J Clin Invest 1998, 101:1633-1642.
3. Kaiser V, Diamond G. Expression of mammalian defensin genes. [In Process Citation]. J Leukoc Biol 2000, 68:779-784.
4. Wachinger M, Kleinschmidt A, Winder D, et al. Antimicrobial peptides melittin and cecropin inhibit replication of human immunodeficiency virus 1 by suppressing viral gene expression. J Gen Virol 1998, 79:731-740.
5. Masuda M, Nakashima H, Ueda T, et al. A novel anti-HIV synthetic peptide, T-22 ([Tyr5,12,Lys7]-polyphemusin II). Biochem Biophys Res Commun 1992, 189:845-850.
6. Oren Z, Shai Y. Mode of action of linear amphipathic alpha-helical antimicrobial peptides. Biopolymers 1998, 47:451-463.
7. Hoover D M, Rajashankar K R, Blumenthal R, et al. The structure of human beta-defensin-2 shows evidence of higher order oligomerization. J Biol Chem 2000, 275:32911-32918.
8. Shai Y. Mechanism of the binding, insertion and destabilization of phospholipid bilayer membranes by alpha-helical antimicrobial and cell non-selective membrane-lytic peptides. Biochim Biophys Acta 1999, 1462:55-70.
9. Isaacs C E, Jia J H, Hillier S. Microbicidal mixtures of octyl glycerol and peptides inactivate HSV. Topical Microbicides Pre-Clinical Workshop III. Baltimore, Md. 2001.
10. Ballweber L M, Jaynes J E, Stamm W E, Lampe M F. In vitro microbicidal activities of cecropin peptides D2A21 and D4E1 and gel formulations containing 0.1 to 2% D2A21 against *Chlamydia trachomatis*. Antimicrob Agents Chemother 2002, 46:34-41.
11. Badkar A, Taliuri K, Tenjaria S, Jaynes J, A. K. B. In vitro release testing of a peptide gel. Pharmaceutical Technology 2000: 47-52.
12. Coleman M S, Rabe L K, Hillier S L. In vitro activity of an antimicrobial peptide for use as an vaginal microbicide. International Congress of Antimicrobial Agents and Chemotherapy 1997.
13. Baghian, A., J. Jaynes, F. Enright, and K. G. Kousoulas. 1997. An amphipathic alpha-helical synthetic peptide analogue of melittin inhibits herpes simplex virus-1 (HSV-1)-induced cell fusion and virus spread. *Peptides* 18:177-183.
14. De Lucca, A. J., J. M. Bland, C. Grimm, T. J. Jacks, J. W. Cary, J. M. Jaynes, T. E. Cleveland, and T. J. Walsh. 1998. Fungicidal properties, sterol binding, and proteolytic resistance of the synthetic peptide D4E1. *Canadian Journal of Microbiology* 44:514-520.
15. Ganz, T. and R. I. Lehrer. 1997. Antimicrobial peptides of leukocytes. [Review] [75 refs]. *Current Opinion in Hematology* 4:53-58.
16. Lehrer, R. I. 1997. Questions and answers about defensins [editorial; comment]. *Clinical Infectious Diseases* 25:1141-1142.
17. Martin, A., H. D. Danforth, J. M. Jaynes, and J. E. Thornton. 1999. Evaluation of the effect of peptidyl membrane-interactive molecules on avian coccidia. *Parasitology Research* 85:331-336.
18. Miyasaki, K. T., R. Iofel, and R. I. Lehrer. 1997. Sensitivity of periodontal pathogens to the bactericidal activity of synthetic protegrins, antibiotic peptides derived from porcine leukocytes. *Journal of Dental Research* 76:1453-1459.
19. Miyasaki, K. T. and R. I. Lehrer. 1998. Beta-sheet antibiotic peptides as potential dental therapeutics. [Review] [81 refs]. *International Journal of Antimicrobial Agents* 9:269-280.
20. Robertson, C. N., K. M. Roberson, A. Pinero, J. M. Jaynes, Paulson, and D F. 1998. Peptidyl membrane-interactive molecules are cytotoxic to prostatic cancer cells in vitro. *World Journal of Urology* 16:405-409.
21. Jaynes J M, C A Burton, S B Barr, G W Jeffers, G R Julian, K L White, F M Enright, T R Klei, and R A Laine. (1988) In Vitro Effect of Novel Lytic Peptides on *Plasmodium falciparum* and *Trypanosoma cruzi*. FASEB. 2(13): 2878-2883.
22. Jaynes J M. (1989) Lytic Peptides: Harbingers of a New Age in the Treatment of Disease. *New Scientist*. 1989: 42-44.
23. Jaynes J M, G W Jeffers, G R Julian, K L White, and F M Enright. (1989) In Vitro Cytocidal Effect of Lytic Peptides on Several Transformed Mammalian Cell Lines. *Peptide Research*. 2(2): 157-160.
24. Jaynes J M. (1990) Lytic Peptides Portend an Innovative Age in the Management and Treatment of Human Disease. *Drug News and Perspectives*. 3(2): 69-78.
25. Kelly D, W Wolters, and J M Jaynes. (1990) The Effect of Lytic Peptides on Fish-Pathogenic Bacteria. *Journal of Fish Diseases*. 13: 317-321.
26. Arrowood M J, J M Jaynes, and M C Healey. (1991) Hemolytic Properties of Lytic Peptides Active Against the Sporozoites of *Cryptosporidium parvum*. *Journal of Protozoology*. 38(6): 161S-163S.
27. Arrowood M J, J M Jaynes, and M C Healy. (1991) In Vitro Activities of Lytic Peptides Against the Sporozoites of *Cryptosporidium parvum*. *Antimicrobial Agents and Chemotherapy*. 35(2):224-227.

28. Miller M A, R F Garry, J M Jaynes, and R C Montelaro. (1991) A Structural Correlation Between Lentivirus Transmembrane Proteins and Natural Cytolytic Peptides. *AIDS Research and Human Retroviruses.* 7(6):511-519.
29. Gunshefski L, M J Mannis, J S Cullor, I R Schwab, J Jaynes, W L Smith, E Mabry, and C J Murphy. (1994) In Vitro Antimicrobial Activity of Shiva-11 Against Ocular Pathogens. *Cornea.* 13(3): 237-42.
30. Barr S C, D Rose, J M Jaynes. (1995) Activity of lytic peptides against intracellular *Trypanosoma cruzi* amastigotes in vitro and parasitemias in mice. *J. Parasitology.* 81(6): 974-978.
31. Sousa L B, M J Mannis, I R Schwab, J Cullor, H Hosotani, W Smith, J Jaynes. (1996). The Use of Synthetic Cecropin (D-5C) in Disinfecting Contact Lens Solutions. *CLAO Journal.* 22(2): 114-117.
32. Baghian A, J Jaynes, F Enright. (1997). An Amphipathic Alpha-Helical Synthetic Peptide Analogue of Melittin Inhibits Herpes Simplex Virus-1 (HSV-1) Induced Cell Fusion and Virus Spread. *Peptides.* 18(2): 177-183.
33. Schwab U, Gilligan P, Jaynes J, Henke D. (1999) In Vitro Activities of Designed Antimicrobial Peptides against Multidrug-Resistant Cystic Fibrosis Pathogens. *Antimicrobial Agents and Chemotherapy.* June 1999, p. 1435-1440.
34. Martin A., Danforth H. D., Jaynes J. M., Thornton J. (1999) Evaluation of the Effect of Peptidyl Membrane-Interactive Molecules on Avian Coccidia. *Parisitology Research* 85: 331-336.
35. Badkar A, Talluri K, Tenjarla S, Jaynes J, Banja A. (2000). In Vitro Release Testing of a Peptide Gel. *Pharmaceutical Technology.* January 2000: 44-51.
36. Arlotti J A, T S Cimino, T S Nguyen, R Dhir, A Thomas, J M Jaynes, A L Caldwell, R H Getzenberg. (2001). Efficacy of a Synthetic Lytic Peptide in the Treatment of Prostate Cancer. *Urologic Oncology* 6: 97-102.
37. Ballweber L M, Jaynes J M, Stamm W E, Lampe M F. In Vitro Microbicidal Activity of Cecropin Peptides D2A21 and D4E1 and Gel Formulations containing 0.1-2.0% D2A21 against *Chlamydia trachomatis.* (2002). *Antimicrobial Agents and Chemotherapy* 46: 34-41.
38. Chalekson C P, Neumeister M W, Jaynes J M. (2002). Treatment of Infected Wounds with Antimicrobial Peptide, D2A21 (Demegel). *Plast Reconstr Surg.* 109: 1338-1343.
39. Ma J, Kennedy-Stoskopf S, Jaynes J, and Tompkins W. (2002). Inhibitory Activity of Synthetic Peptide Antibiotics on Feline Immunodeficiency Virus In Vitro. *Journal of Virology.* Vol. 76: 9952-9961.
40. Chalekson C P, Neumeister M W, Jaynes J M. Improvement in Burn wound Infection and survival with Antimicrobial Peptide D2A21. (2003) *Journal of Trauma: Injury, Infection, and Critical Care* 54(4): 770-774.

What is claimed is:

1. A method to topically treat fungal nail infections and athlete's foot, said method comprising a step of applying a solution comprising a lytic peptide selected from the group consisting of SEQ ID NOs: 1, 2, 5-13, 15, 18-31, and 33-44 on the infected nail or skin.

2. The method according to claim 1, wherein the lytic peptide concentration of the solution is between 1 and 100 μM.

3. The method according to claim 2, wherein the lytic peptide concentration of the solution is 75 μM.

4. The method of claim 1, wherein the solution is applied topically on a nail three times a week.

5. A product to treat fungal nail infections and athlete's foot, said product comprising a solution comprising a lytic peptide selected from the group consisting of SEQ ID NO: 1, 2, 5-13, 15, 18-31, and 33-44.

6. The product according to claim 5, wherein the lytic peptide concentration of the solution is between 1 and 100 μM.

7. The product according to claim 6, wherein the lytic peptide concentration of the solution is 75 μM.

8. A kit for treating fungal nail infection and athlete's foot, said kit comprising:
   a) a dry peptide preparation of a lytic peptides selected from the group consisting of SEQ ID NOs: 1, 2, 5-13, 15, 18-31, and 33-44;
   b) an appropriate amount of distilled water to be mixed with the dry peptide preparation to make a solution wherein the lytic peptide concentration of the solution is between 1 and 100 μM and
   c) instructions to combine peptide and water and to use the resulting solution.

9. The kit according to claim 8, wherein the lytic peptide concentration of the solution is 75 μM.

* * * * *

```
                        SEQUENCE LISTING

<160> NUMBER OF SEQ ID NOS: 44

<210> SEQ ID NO 1
<211> LENGTH: 23
<212> TYPE: PRT
<213> ORGANISM: artificial sequence
<220> FEATURE:
<223> OTHER INFORMATION: chemically synthesized

<400> SEQUENCE: 1

Ala Phe Lys Lys Ala Phe Lys Lys Ala Lys Lys Ala Phe Lys Lys Ala
1               5                   10                  15

Phe Lys Ala Phe Ala Phe Ala
            20

<210> SEQ ID NO 2
<211> LENGTH: 23
<212> TYPE: PRT
<213> ORGANISM: artificial sequence
<220> FEATURE:
<223> OTHER INFORMATION: chemically  synthesized

<400> SEQUENCE: 2

Phe Ala Lys Arg Phe Val Lys Lys Phe Arg Arg Phe Ile Lys Lys Phe
1               5                   10                  15

Leu Arg Phe Ala Phe Val Phe
            20

<210> SEQ ID NO 3
<211> LENGTH: 23
<212> TYPE: PRT
<213> ORGANISM: artificial sequence
<220> FEATURE:
<223> OTHER INFORMATION: chemically synthesized
```

```
<400> SEQUENCE: 3

Phe Ala Lys Lys Phe Ala Lys Lys Phe Lys Lys Phe Ala Lys Lys Phe
1               5                   10                  15

Ala Lys Phe Ala Phe Ala Phe
            20

<210> SEQ ID NO 4
<211> LENGTH: 17
<212> TYPE: PRT
<213> ORGANISM: artificial sequence
<220> FEATURE:
<223> OTHER INFORMATION: chemically synthesized

<400> SEQUENCE: 4

Phe Lys Leu Arg Ala Lys Ile Lys Val Arg Leu Arg Ala Lys Ile Lys
1               5                   10                  15

Leu

<210> SEQ ID NO 5
<211> LENGTH: 38
<212> TYPE: PRT
<213> ORGANISM: artificial sequence
<220> FEATURE:
<223> OTHER INFORMATION: chemically synthesized

<400> SEQUENCE: 5

Phe Lys Leu Arg Ala Lys Ile Lys Val Arg Leu Arg Ala Lys Ile Lys
1               5                   10                  15

Leu Gly Pro Gly Arg Phe Lys Leu Arg Ala Lys Ile Lys Val Arg Leu
            20                  25                  30

Arg Ala Lys Ile Lys Leu
        35

<210> SEQ ID NO 6
<211> LENGTH: 17
<212> TYPE: PRT
<213> ORGANISM: artificial sequence
<220> FEATURE:
<223> OTHER INFORMATION: chemically synthesized

<400> SEQUENCE: 6

Phe Arg Val Lys Ala Arg Ile Arg Leu Lys Val Lys Ala Arg Ile Arg
1               5                   10                  15

Leu

<210> SEQ ID NO 7
<211> LENGTH: 38
<212> TYPE: PRT
<213> ORGANISM: artificial sequence
<220> FEATURE:
<223> OTHER INFORMATION: chemically synthesized

<400> SEQUENCE: 7

Phe Arg Val Lys Ala Arg Ile Arg Leu Lys Val Lys Ala Arg Ile Arg
1               5                   10                  15

Leu Gly Pro Gly Arg Phe Arg Val Lys Ala Arg Ile Arg Leu Lys Val
            20                  25                  30

Lys Ala Arg Ile Arg Leu
        35

<210> SEQ ID NO 8
<211> LENGTH: 24
```

```
<212> TYPE: PRT
<213> ORGANISM: artificial sequence
<220> FEATURE:
<223> OTHER INFORMATION: chemically synthesized

<400> SEQUENCE: 8

Arg Gly Asp Gly Gly Gly Gly Phe Arg Val Lys Ala Arg Ile Arg Leu
1               5                   10                  15

Lys Val Lys Ala Arg Ile Arg Leu
            20

<210> SEQ ID NO 9
<211> LENGTH: 21
<212> TYPE: PRT
<213> ORGANISM: artificial sequence
<220> FEATURE:
<223> OTHER INFORMATION: chemically synthesized

<400> SEQUENCE: 9

Phe Arg Val Lys Ala Arg Ile Arg Leu Lys Val Lys Ala Arg Ile Arg
1               5                   10                  15

Leu Lys Arg Lys Arg
            20

<210> SEQ ID NO 10
<211> LENGTH: 20
<212> TYPE: PRT
<213> ORGANISM: artificial sequence
<220> FEATURE:
<223> OTHER INFORMATION: chemically synthesized

<400> SEQUENCE: 10

Arg Gly Asp Phe Arg Val Lys Ala Arg Ile Arg Leu Lys Val Lys Ala
1               5                   10                  15

Arg Ile Arg Leu
            20

<210> SEQ ID NO 11
<211> LENGTH: 28
<212> TYPE: PRT
<213> ORGANISM: artificial sequence
<220> FEATURE:
<223> OTHER INFORMATION: chemically synthesized

<400> SEQUENCE: 11

Ala Val Lys Arg Val Gly Arg Arg Leu Lys Lys Leu Ala Arg Lys Ile
1               5                   10                  15

Ala Arg Leu Gly Val Ala Lys Leu Ala Gly Leu Phe
            20                  25

<210> SEQ ID NO 12
<211> LENGTH: 17
<212> TYPE: PRT
<213> ORGANISM: artificial sequence
<220> FEATURE:
<223> OTHER INFORMATION: chemically synthesized

<400> SEQUENCE: 12

Met Cys Lys Leu Arg Phe Arg Gly Pro Gly Arg Ile Lys Val Arg Leu
1               5                   10                  15

Cys

<210> SEQ ID NO 13
<211> LENGTH: 25
```

<212> TYPE: PRT
<213> ORGANISM: artificial sequence
<220> FEATURE:
<223> OTHER INFORMATION: chemically synthesized

<400> SEQUENCE: 13

Lys Lys Phe Ala Lys Lys Phe Lys Lys Phe Ala Lys Lys Phe Ala Lys
1               5                   10                  15
Phe Ala Lys Lys Phe Ala Phe Ala Phe
            20                  25

<210> SEQ ID NO 14
<211> LENGTH: 21
<212> TYPE: PRT
<213> ORGANISM: artificial sequence
<220> FEATURE:
<223> OTHER INFORMATION: chemically synthesized

<400> SEQUENCE: 14

Lys Lys Phe Ala Lys Lys Phe Lys Lys Phe Ala Lys Lys Phe Ala Lys
1               5                   10                  15
Phe Ala Phe Ala Phe
            20

<210> SEQ ID NO 15
<211> LENGTH: 25
<212> TYPE: PRT
<213> ORGANISM: artificial sequence
<220> FEATURE:
<223> OTHER INFORMATION: chemically synthesized

<400> SEQUENCE: 15

Phe Ala Phe Ala Phe Lys Lys Ala Phe Lys Ala Phe Lys Lys Ala Phe
1               5                   10                  15
Lys Lys Phe Lys Lys Ala Phe Lys Lys
            20                  25

<210> SEQ ID NO 16
<211> LENGTH: 21
<212> TYPE: PRT
<213> ORGANISM: artificial sequence
<220> FEATURE:
<223> OTHER INFORMATION: chemically synthesized

<400> SEQUENCE: 16

Phe Ala Phe Ala Phe Lys Ala Phe Lys Lys Ala Phe Lys Lys Phe Lys
1               5                   10                  15
Lys Ala Phe Lys Lys
            20

<210> SEQ ID NO 17
<211> LENGTH: 23
<212> TYPE: PRT
<213> ORGANISM: artificial sequence
<220> FEATURE:
<223> OTHER INFORMATION: chemically synthesized

<400> SEQUENCE: 17

Phe Ala Phe Ala Phe Lys Ala Phe Lys Lys Ala Phe Lys Lys Phe Lys
1               5                   10                  15
Lys Ala Phe Lys Lys Ala Phe
            20

<210> SEQ ID NO 18

-continued

```
<211> LENGTH: 23
<212> TYPE: PRT
<213> ORGANISM: artificial sequence
<220> FEATURE:
<223> OTHER INFORMATION: chemically synthesized

<400> SEQUENCE: 18

Ala Phe Ala Phe Ala Lys Phe Ala Lys Lys Phe Ala Lys Lys Ala Lys
1               5                   10                  15

Lys Phe Ala Lys Lys Phe Ala
            20

<210> SEQ ID NO 19
<211> LENGTH: 23
<212> TYPE: PRT
<213> ORGANISM: artificial sequence
<220> FEATURE:
<223> OTHER INFORMATION: chemically synthesized

<400> SEQUENCE: 19

Phe Val Phe Ala Phe Arg Leu Phe Lys Lys Ile Phe Arg Arg Phe Lys
1               5                   10                  15

Lys Val Phe Arg Lys Ala Phe
            20

<210> SEQ ID NO 20
<211> LENGTH: 50
<212> TYPE: PRT
<213> ORGANISM: artificial sequence
<220> FEATURE:
<223> OTHER INFORMATION: chemically synthesized

<400> SEQUENCE: 20

Phe Ala Phe Ala Phe Lys Ala Phe Lys Lys Ala Phe Lys Lys Phe Lys
1               5                   10                  15

Lys Ala Phe Lys Lys Ala Phe Gly Pro Gly Arg Phe Ala Lys Lys Phe
            20                  25                  30

Ala Lys Lys Phe Lys Lys Phe Ala Lys Phe Ala Lys Phe Ala Phe
        35                  40                  45

Ala Phe
    50

<210> SEQ ID NO 21
<211> LENGTH: 53
<212> TYPE: PRT
<213> ORGANISM: artificial sequence
<220> FEATURE:
<223> OTHER INFORMATION: chemically synthesized

<400> SEQUENCE: 21

Ala Phe Ala Phe Lys Lys Ala Phe Lys Ala Phe Lys Lys Ala Phe Lys
1               5                   10                  15

Lys Phe Lys Lys Ala Phe Lys Lys Gly Pro Gly Arg Lys Lys Phe Ala
            20                  25                  30

Lys Lys Phe Lys Lys Phe Ala Lys Lys Phe Ala Lys Phe Ala Lys Lys
        35                  40                  45

Phe Ala Phe Ala Phe
    50

<210> SEQ ID NO 22
<211> LENGTH: 46
<212> TYPE: PRT
<213> ORGANISM: artificial sequence
```

```
<220> FEATURE:
<223> OTHER INFORMATION: chemically synthesized

<400> SEQUENCE: 22

Phe Ala Phe Ala Phe Lys Ala Phe Lys Lys Ala Phe Lys Lys Phe Lys
1               5                   10                  15

Lys Ala Phe Lys Lys Gly Pro Gly Arg Lys Lys Phe Ala Lys Lys Phe
            20                  25                  30

Lys Lys Phe Ala Lys Lys Phe Ala Lys Phe Ala Phe Ala Phe
        35                  40                  45

<210> SEQ ID NO 23
<211> LENGTH: 50
<212> TYPE: PRT
<213> ORGANISM: artificial sequence
<220> FEATURE:
<223> OTHER INFORMATION: chemically synthesized

<400> SEQUENCE: 23

Ala Phe Ala Phe Ala Lys Phe Ala Lys Lys Phe Ala Lys Lys Ala Lys
1               5                   10                  15

Lys Phe Ala Lys Lys Phe Ala Gly Pro Gly Arg Ala Phe Lys Lys Ala
            20                  25                  30

Phe Lys Lys Ala Lys Lys Ala Phe Lys Lys Ala Phe Lys Ala Phe Ala
        35                  40                  45

Phe Ala
    50

<210> SEQ ID NO 24
<211> LENGTH: 50
<212> TYPE: PRT
<213> ORGANISM: artificial sequence
<220> FEATURE:
<223> OTHER INFORMATION: chemically synthesized

<400> SEQUENCE: 24

Phe Val Phe Ala Phe Arg Leu Phe Lys Lys Ile Phe Arg Arg Phe Lys
1               5                   10                  15

Lys Val Phe Arg Lys Ala Phe Gly Pro Gly Arg Phe Ala Lys Arg Phe
            20                  25                  30

Val Lys Lys Phe Arg Arg Phe Ile Lys Lys Phe Leu Arg Phe Ala Phe
        35                  40                  45

Val Phe
    50

<210> SEQ ID NO 25
<211> LENGTH: 50
<212> TYPE: PRT
<213> ORGANISM: artificial sequence
<220> FEATURE:
<223> OTHER INFORMATION: chemically synthesized

<400> SEQUENCE: 25

Phe Ala Lys Lys Phe Ala Lys Lys Phe Lys Lys Phe Ala Lys Lys Phe
1               5                   10                  15

Ala Lys Phe Ala Phe Ala Phe Gly Pro Gly Arg Phe Ala Phe Ala Phe
            20                  25                  30

Lys Ala Phe Lys Lys Ala Phe Lys Lys Phe Lys Lys Ala Phe Lys Lys
        35                  40                  45

Ala Phe
    50
```

```
<210> SEQ ID NO 26
<211> LENGTH: 38
<212> TYPE: PRT
<213> ORGANISM: artificial sequence
<220> FEATURE:
<223> OTHER INFORMATION: chemically synthesized

<400> SEQUENCE: 26

Phe Arg Val Lys Ala Arg Ile Arg Leu Lys Val Lys Ala Arg Ile Arg
1               5                   10                  15

Leu Gly Pro Gly Arg Phe Arg Val Lys Ala Arg Ile Arg Leu Lys Val
            20                  25                  30

Lys Ala Arg Ile Arg Leu
                35

<210> SEQ ID NO 27
<211> LENGTH: 44
<212> TYPE: PRT
<213> ORGANISM: artificial sequence
<220> FEATURE:
<223> OTHER INFORMATION: chemically synthesized

<400> SEQUENCE: 27

Phe Arg Val Lys Ala Arg Ile Arg Leu Lys Val Lys Ala Arg Ile Arg
1               5                   10                  15

Leu Gly Pro Gly Arg Phe Ala Lys Arg Phe Val Lys Lys Phe Arg Arg
            20                  25                  30

Phe Ile Lys Lys Phe Leu Arg Phe Ala Phe Val Phe
            35                  40

<210> SEQ ID NO 28
<211> LENGTH: 35
<212> TYPE: PRT
<213> ORGANISM: artificial sequence
<220> FEATURE:
<223> OTHER INFORMATION: chemically synthesized

<400> SEQUENCE: 28

Asn Cys Gly Pro Cys Lys Gly Gly Gly Lys Lys Phe Ala Lys Lys
1               5                   10                  15

Phe Lys Lys Phe Ala Lys Lys Phe Ala Lys Phe Ala Lys Lys Phe Ala
            20                  25                  30

Phe Ala Phe
        35

<210> SEQ ID NO 29
<211> LENGTH: 35
<212> TYPE: PRT
<213> ORGANISM: artificial sequence
<220> FEATURE:
<223> OTHER INFORMATION: chemically synthesized

<400> SEQUENCE: 29

Lys Lys Phe Ala Lys Lys Phe Lys Lys Phe Ala Lys Lys Phe Ala Lys
1               5                   10                  15

Phe Ala Lys Lys Phe Ala Phe Ala Phe Gly Gly Gly Gly Asn Cys Gly
            20                  25                  30

Pro Cys Lys
        35

<210> SEQ ID NO 30
```

```
<211> LENGTH: 54
<212> TYPE: PRT
<213> ORGANISM: artificial sequence
<220> FEATURE:
<223> OTHER INFORMATION: chemically synthesized

<400> SEQUENCE: 30

Ala Phe Ala Phe Lys Lys Ala Phe Lys Ala Phe Lys Lys Ala Phe Lys
1               5                   10                  15

Lys Phe Lys Lys Ala Phe Lys Lys Gly Pro Gly Arg Lys Lys Phe Ala
            20                  25                  30

Lys Lys Phe Lys Lys Phe Ala Lys Lys Phe Ala Lys Phe Ala Lys Lys
        35                  40                  45

Phe Ala Phe Ala Phe Cys
    50

<210> SEQ ID NO 31
<211> LENGTH: 23
<212> TYPE: PRT
<213> ORGANISM: artificial sequence
<220> FEATURE:
<223> OTHER INFORMATION: chemically synthesized

<400> SEQUENCE: 31

Trp Phe Lys Lys Ala Phe Lys Lys Ala Lys Lys Ala Phe Lys Lys Ala
1               5                   10                  15

Phe Lys Ala Phe Ala Phe Ala
            20

<210> SEQ ID NO 32
<211> LENGTH: 23
<212> TYPE: PRT
<213> ORGANISM: artificial sequence
<220> FEATURE:
<223> OTHER INFORMATION: chemically synthesized

<400> SEQUENCE: 32

Phe Leu Phe Ala Phe Arg Ile Phe Lys Arg Val Phe Lys Lys Phe Arg
1               5                   10                  15

Lys Leu Phe Lys Arg Ala Phe
            20

<210> SEQ ID NO 33
<211> LENGTH: 18
<212> TYPE: PRT
<213> ORGANISM: artificial sequence
<220> FEATURE:
<223> OTHER INFORMATION: chemically synthesized

<400> SEQUENCE: 33

Met Gly Cys Lys Leu Arg Phe Arg Gly Pro Gly Arg Ile Lys Val Arg
1               5                   10                  15

Leu Cys

<210> SEQ ID NO 34
<211> LENGTH: 19
<212> TYPE: PRT
<213> ORGANISM: artificial sequence
<220> FEATURE:
<223> OTHER INFORMATION: chemically synthesized

<400> SEQUENCE: 34

Met Gly Phe Lys Leu Arg Ala Lys Ile Lys Val Arg Leu Arg Ala Lys
1               5                   10                  15
```

Ile Lys Leu

<210> SEQ ID NO 35
<211> LENGTH: 19
<212> TYPE: PRT
<213> ORGANISM: artificial sequence
<220> FEATURE:
<223> OTHER INFORMATION: chemically synthesized

<400> SEQUENCE: 35

Met Gly Phe Arg Val Lys Ala Arg Ile Arg Leu Lys Val Lys Ala Arg
1               5                   10                  15

Ile Arg Leu

<210> SEQ ID NO 36
<211> LENGTH: 42
<212> TYPE: PRT
<213> ORGANISM: artificial sequence
<220> FEATURE:
<223> OTHER INFORMATION: chemically synthesized

<400> SEQUENCE: 36

Met Gly Phe Lys Leu Arg Ala Lys Ile Lys Val Arg Leu Arg Ala Lys
1               5                   10                  15

Ile Lys Leu Gly Pro Gly Arg Met Gly Phe Lys Leu Arg Ala Lys Ile
            20                  25                  30

Lys Val Arg Leu Arg Ala Lys Ile Lys Leu
        35                  40

<210> SEQ ID NO 37
<211> LENGTH: 42
<212> TYPE: PRT
<213> ORGANISM: artificial sequence
<220> FEATURE:
<223> OTHER INFORMATION: chemically synthesized

<400> SEQUENCE: 37

Met Gly Phe Arg Val Lys Ala Arg Ile Arg Leu Lys Val Lys Ala Arg
1               5                   10                  15

Ile Arg Leu Gly Pro Gly Arg Met Gly Phe Arg Val Lys Ala Arg Ile
            20                  25                  30

Arg Leu Lys Val Lys Ala Arg Ile Arg Leu
        35                  40

<210> SEQ ID NO 38
<211> LENGTH: 12
<212> TYPE: PRT
<213> ORGANISM: artificial sequence
<220> FEATURE:
<223> OTHER INFORMATION: chemically synthesized
<220> FEATURE:
<221> NAME/KEY: MISC_FEATURE
<222> LOCATION: (3)..(3)
<223> OTHER INFORMATION: Xaa is Ornithine
<220> FEATURE:
<221> NAME/KEY: MISC_FEATURE
<222> LOCATION: (8)..(8)
<223> OTHER INFORMATION: Xaa is Ornithine

<400> SEQUENCE: 38

Cys Val Xaa Leu Phe Pro Val Xaa Leu Phe Pro Cys
1               5                   10

<210> SEQ ID NO 39

```
<211> LENGTH: 12
<212> TYPE: PRT
<213> ORGANISM: artificial sequence
<220> FEATURE:
<223> OTHER INFORMATION: chemically synthesized

<400> SEQUENCE: 39

Cys Val Lys Leu Phe Pro Val Lys Leu Phe Pro Cys
1               5                   10

<210> SEQ ID NO 40
<211> LENGTH: 12
<212> TYPE: PRT
<213> ORGANISM: artificial sequence
<220> FEATURE:
<223> OTHER INFORMATION: chemically synthesized
<220> FEATURE:
<221> NAME/KEY: MISC_FEATURE
<222> LOCATION: (2)..(2)
<223> OTHER INFORMATION: Xaa is Ornithine

<400> SEQUENCE: 40

Cys Xaa Leu Phe Pro Phe Phe Asp Glu Tyr Val Cys
1               5                   10

<210> SEQ ID NO 41
<211> LENGTH: 12
<212> TYPE: PRT
<213> ORGANISM: artificial sequence
<220> FEATURE:
<223> OTHER INFORMATION: chemically synthesized

<400> SEQUENCE: 41

Cys Lys Leu Phe Pro Phe Phe Asp Glu Tyr Val Cys
1               5                   10

<210> SEQ ID NO 42
<211> LENGTH: 16
<212> TYPE: PRT
<213> ORGANISM: artificial sequence
<220> FEATURE:
<223> OTHER INFORMATION: chemically synthtesized

<400> SEQUENCE: 42

Cys Lys Leu Arg Phe Arg Gly Pro Gly Arg Ile Lys Val Arg Leu Cys
1               5                   10                  15

<210> SEQ ID NO 43
<211> LENGTH: 12
<212> TYPE: PRT
<213> ORGANISM: artificial sequence
<220> FEATURE:
<223> OTHER INFORMATION: chemically synthesized

<400> SEQUENCE: 43

Cys Lys Leu Arg Phe Arg Ile Lys Val Arg Leu Cys
1               5                   10

<210> SEQ ID NO 44
<211> LENGTH: 26
<212> TYPE: PRT
<213> ORGANISM: artificial sequence
<220> FEATURE:
```

```
-continued

<223> OTHER INFORMATION: chemically synthesized

<400> SEQUENCE: 44

Cys Pro Gly Phe Ala Lys Lys Phe Ala Lys Lys Phe Lys Lys Phe Ala
1               5                   10                  15

Lys Lys Phe Ala Lys Phe Ala Phe Ala Phe
            20                  25
```